United States Patent [19]

Schroeder et al.

[11] Patent Number: 4,892,972
[45] Date of Patent: Jan. 9, 1990

[54] PURIFICATION OF CRUDE TEREPHTHALIC ACID

[75] Inventors: Hobe Schroeder, Warrenville; David E. James, Batavia, both of Ill.

[73] Assignee: Amoco Corporation, Chicago, Ill.

[21] Appl. No.: 344,657

[22] Filed: Apr. 27, 1989

Related U.S. Application Data

[63] Continuation of Ser. No. 905,766, Sep. 10, 1986, abandoned, which is a continuation-in-part of Ser. No. 785,322, Oct. 7, 1985, abandoned.

[51] Int. Cl.$^4$ .......................... C07C 51/42; B01J 21/18
[52] U.S. Cl. ..................................... 562/487; 502/185; 562/485; 562/486
[58] Field of Search ................ 502/185; 562/485, 486, 562/487

[56] References Cited

U.S. PATENT DOCUMENTS

| | | | |
|---|---|---|---|
| 3,546,285 | 12/1970 | Witt | 562/487 |
| 3,584,039 | 6/1971 | Meyer | 562/487 |
| 3,639,465 | 2/1972 | Olsen et al. | 562/487 |
| 3,726,915 | 4/1973 | Pohlmann | 562/487 |
| 4,126,638 | 11/1978 | Alagy et al. | 562/487 |
| 4,405,809 | 9/1983 | Stech et al. | 562/487 |
| 4,467,110 | 8/1984 | Puskas et al. | 562/487 |

FOREIGN PATENT DOCUMENTS 1578725 11/1980 United Kingdom .

Primary Examiner—Werren B. Lone
Assistant Examiner—Vera C. Clarke
Attorney, Agent, or Firm—James R. Henes; William H. Magidson; Ralph C. Medhurst

[57] ABSTRACT

Aqueous solutions of crude terephthalic acid are purified by hydrogenation in the presence of plural noble metal catalysts in separate layers. Initially, the solution to be purified is passed through a layer of ruthenium-on-carbon catalyst, rhodium-on-carbon catalyst, or platinum-on-carbon catalyst, and thereafter through a layer of palladium-on-carbon catalyst. Optionally, the purified aqueous terephthalic acid solution can be treated further to decrease the 4-carboxybenzaldehyde content thereof by passing it through a layer of rhodium-on-carbon catalyst downstream from the palladium-on-carbon catalyst layer.

30 Claims, 2 Drawing Sheets

PURIFICATION OF CRUDE TEREPHTHALIC ACID

This is a continuation of application Ser. No. 905,766, filed Sept. 10, 1986, now abandoned, which in turn is a continuation-in-part application of U.S. patent application Ser. No. 785,322 which was filed on Oct. 7, 1985, now abandoned.

BACKGROUND OF THE INVENTION

1. Field of the Invention

This invention relates generally to a method for the catalytic purification of crude terephthalic acid and to the catalyst system employed therein, and more particularly concerns a layered catalyst bed and its use in such purification.

2. Discussion of the Prior Art

Polymer grade or "purified" terephthalic acid is the starting material for polyethylene terephthalate, which is the principal polymer for use in the manufacture of polyester fibers, polyester films, and resins for bottles and like containers.

Purified terephthalic acid is derived from relatively less pure, technical grade or "crude" terephthalic acid by purification of the latter utilizing hydrogen and a noble metal catalyst as described in Meyer, U.S. Pat. No. 3,584,039 or Stech et al., U.S. Pat. No. 4,405,809. In the purification process, the crude terephthalic acid is dissolved in water at an elevated temperature, and the resulting solution is hydrogenated, preferably in the presence of a hydrogenation catalyst containing a noble metal, typically palladium, on a carbon support, as described in Pohlmann, U.S. Pat. No. 3,726,915. This hydrogenation step converts the various color bodies present in the crude terephthalic acid to colorless products.

However, even after purification, the purified terephthalic acid product contains color bodies. It is highly desirable to reduce the concentration of such color bodies that remain in purified terephthalic acid. The color level of purified terephthalic acid product is generally measured directly either by measuring the optical density of solutions of purified terephthalic acid or the b*-value of the solid purified terephthalic acid itself. The optical density of purified terephthalic acid is measured as the absorbance of light at 340 nanometers in its basic solution in a solvent such as sodium hydroxide or ammonium hydroxide.

The measurement of the b*-value of a solid on the Hunter Color Scale is described in Hunter, *The Measurement of Appearance*, Chapter 8, pp. 102-132, John Wiley & Sons, N.Y., N.Y. (1975), and in Wyszecki et al., *Color Science, Concepts and Methods, Quantitative Data and Formulae*, 2d Ed., pp. 166-168, John Wiley & Sons, N.Y., N.Y. (1982).

More specifically, the b*-value of purified terephthalic acid can be determined using, for example, a Diano Match Scan Spectrophotometer as follows. Purified terephthalic acid is pressed into a pellet having a thickness of about 0.25 inch and a diameter of about 1 inch. The pellet is then irradiated with white light that has been UV-filtered. The spectrum of the visible light reflected from the sample is determined and tristimulus values (X, Y. and Z) are computed using the CIE Standard Observer functions. Using the weighted-ordinate method, tristimulus values are obtained from the following equations:

$$X = \sum_{400}^{700} R_\lambda \bar{x}_\lambda, \ Y = \sum_{400}^{700} R_\lambda \bar{y}_\lambda, \ Z = \sum_{400}^{700} R_\lambda \bar{z}_\lambda,$$

where $R_\lambda$ is the percent reflectance of the object at wavelength $\lambda$ and $\bar{x}_\lambda$, $\bar{y}_\lambda$, and $\bar{z}_\lambda$ are the Standard Observer functions at wavelength $\lambda$ for CIE Illuminant D65. The tristimulus values, X, Y and Z, identify the color of the object in terms of the mixture of the primary lights that match it visually. Tristimulus values, however, are of limited use as color specifications, because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts tristimulus values to L*, a*, and b* values as shown below:

$L^* = 25(100Y/Y_o)^{\frac{1}{3}} - 16$
$a^* = 500[(X/X_o)^{\frac{1}{3}} - (Y/Y_o)^{\frac{1}{3}}]$
$b^* = 200[(Y/Y_o)^{\frac{1}{3}} - (Z/Z_o)^{\frac{1}{3}}]$ The L*-value is a measure of the luminosity or whiteness of an object where L* = 100 is pure white, L* = 0 is black, and in between in gray. The L*-value is strictly a function of the tristimulus Y-value. The b*-value is a measure of the yellowness-blueness attribute where positive b*-value represent yellow appearance and negative b*-values represent blue appearance. The b*-value is a function of both tristimulus values Y and Z.

Furthermore, even after purification, the purified terephthalic acid product often contains impurities which fluoresce at wavelengths of 390-400 nanometers upon excitation at wavelengths of 260-320 nanometers. Further reduction of such fluorescence of the purified terephthalic acid product is highly desirable. Since the concentration of such impurities in purified terephthalic acid can vary significantly, specifications are often established for the amount of such fluorescence which can be permitted for the purified terephthalic acid product. The problem of the control of such fluorescence by purified terephthalic acid is complicated because some of the fluorescent impurities are soluble and can be removed by conventional procedures for purifying terephthalic acid while other such fluorescent impurities are insoluble and cannot be removed by such conventional procedures. Furtheremore, upon chemical reduction during purification of crude terephthalic acid, some impurities which do not themselves fluoresce at wavelengths of 390-400 nanometers upon excitation at wavelengths of 260-320 nanometers are converted to their reduced forms which fluoresce at 390-400 nanometers upon excitation by wavelengths of 260-320 nanometers.

Puskas et al., U.S. Pat. Nos. 4,394,299 and 4,467,110 disclose the use of a combination noble metal catalyst, for example, a palladium/rhodium catalyst on a porous carbonaceous surface, for purification of aqueous terephthalic acid solutions. These two patents also show the use of a rhodium-on-carbon catalyst under reducing conditions and review various heretofore known methods of preparing a Group VIII metal catalyst having activity and selectivity suitable for the purification of terephthalic acid by hydrogenating its principal impurity, 4-carboxybenzaldehyde, to p-toluic acid.

However, p-toluic acid is also an impurity that must be removed from the hydrogenated aqueous terephthalic solution. While such removal can be achieved to a large extent owing to the greater solubility of p-toluic acid as compared to terephthalic acid, in water nevertheless substantial amounts of p-toluic acid are trapped within purified terephthalic acid crystals as the hydrogenated terephthalic acid solution is crystallized to recover purified terephthalic acid.

To avoid the disadvantages attendant to the separation of p-toluic acid, it has been proposed to decarbonylate 4-carboxybenzaldehyde in aqueous solutions to benzoic acid in the presence of a palladium-on-carbon catalyst but without the simultaneous hydrogenation of the other impurities that may be present in aqueous solutions of crude terephthalic acid since benzoic acid is more soluble in water then p-toluic acid. See, for example, Olsen, U.S. Pat. No. 3,456,001.

However, the foregoing decarbonylation of 4-carboxybenzaldehyde to benzoic acid produces equimolar amounts of carbon monoxide, a well-known poison for the noble metals such as palladium (see, for example, Kimura et al., U.S. Pat. No. 4,201,872). In any attempt to minimize catalyst poisoning, Kimura et al., in the aforementioned patent, propose to carry out the decarbonylation at relatively low process pressures so as to minimize dissolved carbon monoxide concentration in the liquid reaction medium. The process pressures also must be controlled within a closely defined pressure range. The generated carbon monoxide is purged from the reactor as a gas.

We have now discovered that the use in the aforesaid purification of crude terephthalic acid of a catalyst system comprising a first layer of catalyst particles containing a metal of Group VIII of the Periodic Table of Elements having a single electron in its outermost orbital when in the ground state supported on a carbon carrier and a second layer of palladium-on-carbon catalyst particles and the passage of the aqueous solution of crude terephthalic acid through the aforesaid first layer of rhodium-on-carbon catalyst particles and then through the second layer of palladium-on-carbon catalyst particles permits the amount of p-toluic acid produced during purification of crude terephthalic acid to be minimized. Such method of using the aforesaid catalyst system does not promote the hydrogenation of 4-carboxybenzaldehyde to p-toluic acid but instead promotes the decarbonylation of 4-carboxybenzaldehyde to benzoic acid, which is more soluble than p-toluic acid in water and thus is more readily separable than p-toluic acid from terephthalic acid upon crystallization of the terephthalic acid. This permits a feed solution having a relatively higher 4-carboxybenzaldehyde content to be processed economically. In addition, such benefits are attained without the aforesaid deleterious effects on the catalyst system caused by the generated carbon monoxide.

Furthermore, we have also discovered that such method of using the aforesaid catalyst system effects a further decrease in the concentration of color bodies and of fluorescent impurities in the resulting purified terephthalic acid, relative to the use of a conventional palladium-on-carbon catalyst alone.

SUMMARY OF THE INVENTION

The present invention contemplates the purification of relatively impure aqueous solutions of crude terephthalic acid by hydrogenation in the presence of plural noble metal catalysts in separate layers. Substantial conversion of 4-carboxybenzaldehyde to benzoic acid is obtained concurrently with a Fischer-Tropsch type of reaction in the same reaction vessel that converts generated carbon monoxide to a hydrocarbon moiety such as methane, ethane, or the like. Terephthalic acid of relatively high purity and having relatively reduced contents of color bodies and fluorescent impurities can be produced in this manner. If desired, the produced benzoic acid can be recovered as a commercially valuable by-product.

According to the present invention, a relatively impure aqueous terephthalic acid solution, preferably containing up to about 10,000 parts of 4-carboxybenzaldehyde per million parts of terephthalic acid, by weight, is hydrogenated in a liquid-filled, layered particulate catalyst bed that contains plural layers of different hydrogenation catalysts. In the catalyst bed, a first catalyst layer is present that includes as a metal catalyst supported on an active carbon carrier, a metal of Group VIII of the Periodic Table of Elements having a single electron in its outermost orbital when in ground state. These metals are ruthenium, rhodium, and platinum. A second catalyst layer is also present in the catalyst bed, downstream from the first layer, and includes palladium supported on an active carbon carrier.

The hydrogenation is carried out at a temperature of about 100° C. to about 350° C. and at a pressure sufficient to maintain the solution in liquid phase, usually about 200 psig to about 1,500 psig, with attendant carbon monoxide generation. The aqueous terephthalic acid solution to be purified is first passed through the first catalyst layer and thereafter through the second catalyst layer, both under reducing conditions, i.e., while in the presence of hydrogen.

the generated carbon monoxide is converted within the reactor to a hydrocarbon such as methane, ethane, or the like. The carbon monoxide conversion also requires hydrogen, thus the amount of hydrogen present in the liquid-filled particulate bed preferably is at least equal to that stoichiometrically required to effect a predetermined decrease in the 4-carboxybenzaldehyde content of the aqueous solution and to convert at least a portion, preferably a major portion, of the generated carbon monoxide to a hydrocarbon moiety.

The hydrogenated aqueous solution, i.e., the liquid effluent from the catalyst bed, is thereafter cooled to effect separation of the resulting purified terephthalic acid from the soluiton by crystallization.

DETAILED DESCRIPTION OF THE DRAWINGS INCLUDING PREFERRED EMBODIMENTS

The method of this invention is particularly suitable for use in the purification of crude terephthalic acid prepared by the continuous catalytic, liquid-phase oxidation of p-xylene in a solvent. Suitable solvents for use in the catalytic, liquid-phase oxidation of p-xylene include any aliphatic $C_2$–$C_6$ monocarboxylic acid such as acetic acid, propionic acid, n-butyric acid, isobutyric acid, n-valeric acid, trimethylacetic acid, and caproic acid, and water and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude terephthalic acid product from the product stream, at least a portion of the mother liquor (solvent) in the resulting product stream is generally recycled to the reactor.

The source of molecular oxygen employed in the oxidation step of the method for producing purified terephthalic acid can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the oxidation step of the method for producing crude terephthalic acid comprises cobalt, manganese, and bromine components, and can additionally comprise accelerators known in the art. The weight ratio of cobalt (calculated as elemental cobalt) in the cobalt component of the catalyst-to-p-xylene in the liquid-phase oxidation is in the range of from about 0.2 to about 10 milligram atoms (mga) per gram mole of p-xylene. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.2 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromine can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

In operation, the minimum pressure at which the oxidation reactor is maintained is that pressure which will maintain a substantial liquid phase of the p-xylene and at least 70 percent of the solvent. The p-xylene and solvent not in the liquid phase because of vaporization are removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm$^2$ to about 35 kg/cm$^2$, and typically are in the range of from about 10 kg/cm$^2$ to about 30 kg/cm$^2$. The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

The resulting product is an aqueous solution or relatively impure or crude terephthalic acid that includes relatively large amounts of impurities such as 4-carboxybenzaldehyde which can be present in amounts up to about 10,000 parts per million parts of terephthalic acid, by weight. These impurities adversely affect terephthalic acid polymerization reactions to produce polyethylene terephthalate as well as cause undesirable coloring of the resulting polyethyleneterephthalate polymers.

The process embodying the present invention is conducted at an elevated temperature and pressure in a fixed catalyst bed that is layered. Both down-flow and up-flow reactors can be used. The crude terephthalic acid to be purified is dissolved in water or a like polar solvent. Water is the preferred solvent; however, other suitable polar solvents are the relatively lower molecular weight alkyl carboxylic acids, alone or admixed with water.

Reactor, and thus terephthalic acid solution, temperatures during purification can be in the range of about 100° C. (about 212° F.) to about 350° C. (about 660° F.). Preferably the temperatures are in the range of about 275° C. (about 530° F.) to about 300° C. (about 572° F.).

Reactor pressure conditions primarily depend upon the temperature at which the purification process is carried out. Inasmuch as the temperatures at which practical amounts of the impure terephthalic acid may be dissolved are substantially above the normal boiling point of the polar sovlent, the process pressures are necessarily considerably above atmospheric pressure to maintain the aqueous solution in liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. The use of an inert gas in admixture with hydrogen also can provide an advantageous menas for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in the range of about 200 to about 1500 pounds per square inch guage (psig), and usually is in the range of about 900 psig to about 1,200 psig.

the hydrogenaton reactor can be operated in several modes. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the terephthalic acid solution present is the hydrogen partial pressure in the reactor vapor space. Alternatively, if hydrogen is fed in admixture with an inert gas such as nitrogen, the difference between the actual reactor pressure and the vapor pressure of the terephthalic acid solution present is the combined partial pressure of hydrogen and the inert gas admixed therewith. In this case the hydrogen partial pressure can be calculated from the known relative amounts of hydrogen and inert gas present in the admixture.

In yet another operating mode, the reactor can be filled with the terephthalic acid solution so as to provide no reactor vapor space. That is, the reactor can be operated as a hydraulically full system with dissolved hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of contamination of the impure terephthalic acid, the activity and age of the particular catalyst employed, and like processing considerations.

In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution. In general, an amount of hydrogen that is sufficient to effect the desired hydrogenation under the reaction conditions employed is supplied to the purification reactor.

In purifying aqueous terephthalic acid solutions that contain 4-carboxybenzaldehyde (4-CBA) according to the present invention, the following principal reactions leading to the formation of p-hydroxymethyl-benzoic acid (HMBA), p-toluic acid (TOL) and benzoic acid (BA) are believed to occur.

Thus, a substantial portion of 4-carboxybenzaldehyde present in the crude terephthalic acid is decarbonylated to benzoic acid while most of the remainder is converted to p-toluic acid in the same reactor. Some decomposition of terephthalic acid to benzoic acid and hydrogenation of terephthalic acid to 4-carboxybenzaldehyde also takes place; however, both of these are minor reactions.

Whereas heretofore the presence of carbon monoxide in a 4-carboxybenzaldehyde hydrogenation reactor was deemed to be a problem because carbon monoxide is known to inhibit the activity of hydrogenation catalysts, the present process avoids this problem by effecting in the reactor a conversion of at least a substantial portion of the generated carbon monoxide to a hydrocarbon moiety, e.g., methane, by what is believed to be a Fischer-Tropsch type of reaction. Preferably, a major portion of the generated carbon monoxide is converted to a hydrocarbon moiety. The produced hydrocarbon by-products are inert with respect to the purified terephthalic acid and can be readily separated from the resulting reaction product admixture by purging or in any other convenient manner.

Decarbonylation and carbon monoxide conversion to a hydrocarbon moiety are believed to occur substantially simultaneously in the first layer of the layered fixed catalyst bed of this invention. The catalyst for the decarbonylation and the carbon monoxide conversion is a carrier-supported metal of Group VIII of the Periodic Table of Elements having a single electron in its outermost orbital when in the ground state. The pertinent Periodic Table of Elements can be found on the inside of the front cover of *Handbook of Chemistry and Physics*, 54th edition, Chemical Rubber Company, Cleveland, Ohio (1973). Rhodium is the preferred catalyst; however, ruthenium and platinum are also suitable. Such catalysts are commercially available.

A suitable palladium-on-carbon catalyst can be obtained, for example, from Engelhard Corporation, Newark, N.J., under the designation "Palladium on Activated Carbon Granules (Carbon Code CG-5)." Similarly, suitable rhodium-on-carbon catalysts can be obtained from Engelhard Corporation, under the designations "Rhodium on Activated Carbon Granules (Carbon Code CG-5)" and "Rhodium on Activated Carbon Granules (Carbon Code CG-21)." Both of these rhodium-on-carbon catalysts have a $N_2$ BET surface area of about 1,000 m²/gram and have a particle size 4×8 mesh, U.S. Sieve Series. Other suitable rhodium-on-carbon catalysts of similar size and surface area are available from Johnson Matthey Inc., Seabrook, N.H., under the designation "11766 Rhodium, 1% on Steam Activated Carbon Granules, Anhydrous."

The catalyst carrier is active carbon, usually that derived from coconut charcoal in the form of granules having a surface area of at least about 600 m²/g ($N_2$; BET Method), preferably about 800 m²/g to about 1,500 m²/g. However, other porous carbonaceous supports or substrates can be used as long as the surface area requirements can be met. In addition to coconut charcoal, activated carbon derived from other plant or from animal sources can be utilized.

Ruthenium, rhodium or platinum loading on the carrier can be in the range of about 0.01 weight percent to about 2 weight percent, based on the total weight of the catalyst, i.e., metal plus active carbon carrier, and calculated as elemental metal. Preferably the catalyst metal loading is about 0.5 weight percent.

Hydrogenation of 4-carboxybenzaldehyde to p-toluic acid is the principal reaction that occurs in the second layer of the layered fixed catalyst bed. This second layer is constituted by a conventional palladium-on-active carbon (Pd/C) particulate catalyst. A typical palladium-on-carbon catalyst comprises about 0.01 to about 2 weight percent of palladium, based on the total weight of the catalyst and calculated as elemental metal. The support or carrier for the palladium is porous and inert, and preferably is active carbon having a surface area of about 600 m²/g to about 1500 m²/gram. Suitable supports for palladium-on-carbon hydrogenation catalysts are well known and are described, inter alia, in U.S. Pat. No. 3,584,039, to Meyer.

The relative thickness of the particulate catalyst layers in the hydrogenation bed can vary; however, the first catalyst layer preferably constitutes a minor portion of the fixed bed and the second catalyst layer constitutes a major portion of the catalyst bed. The first catalyst layer at all times is thick enough to avoid substantial channeling within the catalyst layer as the aqueous crude terephthalic acid feed solution is passed therethrough. To that end, and as a practical matter, whatever the catalyst bed diameter, the first catalyst layer is at least about 25 millimeters (about 1 inch) thick. Volumetrically, the first catalyst layer preferably is about one-tenth the volume of the second, palladium-on-carbon catalyst layer; however, the volumetric ratio of the first catalyst layer to the second catalyst layer can be in the range of about 0.001 to about 1.

The relative amount of catalyst metal in the first catalyst layer and in the second catalyst layer can vary. Generally, the desired Group VIII metal, as defined above, for the first layer and palladium for the second layer are present in a mol ratio of about 1:1 to about 1:1000, preferably in a mol ratio of about 1:10.

The amount of hydrogen supplied under reaction conditions is, of course, sufficient to effect the desired conversion of the generated carbon monoxide to a hydrocarbon and the desired degree of hydrogenation of 4-carboxybenzaldehyde to p-toluic acid. For conversion of 4-carboxybenzaldehyde to p-toluic acid, the stoichiometric hydrogen requirement is two mols of hydrogen for each mol of 4-carboxybenzaldehyde so converted. For conversion of 4-carboxybenzaldehyde to benzoic acid, the stoichiometric hydrogen requirement is due to the generated carbon monoxide. For conversion of all generated carbon monoxide to methane this reuqirement is three mols of hydrogen for each mol of 4-carboxybenzaldehyde converted to benzoic acid. Preferably, the amount of hydrogen supplied to the catalyst bed is about twice that stoichiometrically required for the foregoing principal reactions that are taking place in the catalyst bed.

Preferably, crude terephthalic acid feed to the catalyst bed in the reactor is supplied at a rate sufficient to maintain a p-toluic acid (TOL)-to-benzoic acid (BA) weight ratio of less than about 2.5 in the liquid effluent from the catalyst bed. More preferably, the p-toluic acid-to-benzoic acid weight ratio in the effluent is maintained in a range of about 1.5 to about 0.5.

Space velocity (lbs terephthalic acid solution/lb catalyst/hr) of the aqueous crude terephthalic acid solution through the catalyst bed is about 5 hours$^{-1}$ to about 25 hours$^{-1}$, preferably about 10 hours$^{-1}$ to about 15 hours$^{-1}$. The residence time of the terephthalic acid solution in the catalyst bed varies, depending upon the activity of the catalysts present. In general, however, the residence time of the aqueous terephthalic acid solution in the first catalyst layer is about ½ to about 1/100 of the total residence time of the aqueous terephthalic acid solution in the catalyst bed.

The four principal factors that affect the degree of 4-carboxybenzaldehyde conversion in the catalyst bed are catalyst metal loadings in the catalyst bed, catalyst activity, total layer and bed thicknesses, and feed throughput rate. However, as a practical matter, even under optimized process conditions the 4-carboxybenzaldehyde content of the aqueous liquid effluent from the catalyst bed is nevertheless about 25 to about 50 parts per million parts of terephthalic acid, on a weight basis. While for some end uses of purified TA such a 4-carboxybenzaldehyde content is acceptable, in other instances it is desirable to reduce the 4-carboxybenzaldehyde content of the liquid effluent even further.

To that end, it has been found that the catalyst bed can be provided with an additional, third catalyst layer of particulate rhodium-on-carbon (Rh/C) catalyst downstream of the aforedescribed second catalyst layer. This is more fully described in copending U.S. patent application Ser. No. 785,321, entitled "Purification of Terephthalic Acid to Relatively Low Levels of 4-Carboxybenzaldehyde." The specification of said concurrently filed application is incorporated herein by reference to the extent pertinent.

Briefly, in such an event the particulate rhodium-on-carbon catalyst layer constitutes the last layer through which the feed solution passes before exiting the reactor. This third catalyst layer of the fixed catalyst bed contains about 0.01 to about 2 weight percent of rhodium, based on total weight of the particulate catalyst present in the third layer and calculated as elemental metal.

If a third catalyst layer containing rhodium-on-carbon catalyst is present, that catalyst layer is at least about 50 millimeters thick. That is, the minimum thickness of the third catalyst layer is about twice the minimum thickness of the first catalyst layer in the catalyst bed. The maximum thickness of the third layer can vary depending upon the activity of the particular rhodium-on-carbon catalyst employed, the reactor throughput rate, the thickness of the first catalyst layer, the 4-carboxybenzaldehyde content of the incoming feed solution, and like considerations. However, at all times the third catalyst layer constitutes less than one-half of the total catalyst bed thickness, i.e., it constitutes a minor portion of the total catalyst bed thickness.

Figure 1:
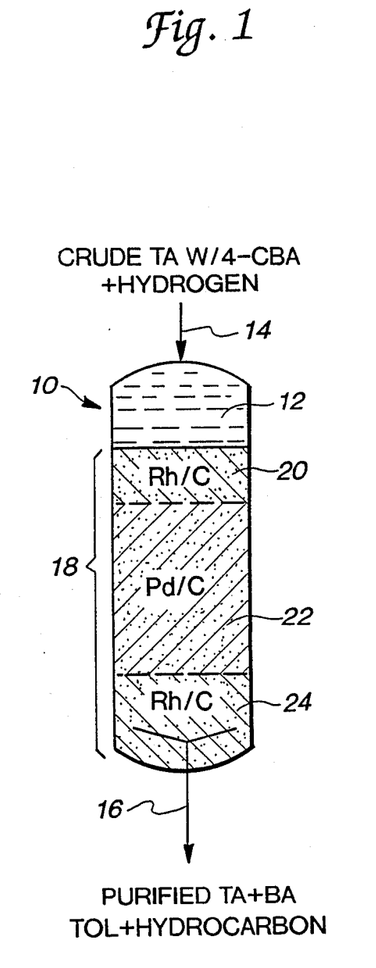
FIG. 1 is a diagrammatic depiction of a reactor having a layered particulate catalyst bed embodying the present invention.

A layered catalyst bed suitable for hydrogenation of a relatively impure aqueous solution of terephthalic acid containing 4-carboxybenzaldehyde is shown in FIG. 1. Down-flow reactor 10 is shown hydraulically full with crude aqueous terephthalic acid solution 12 that is to be purified. This feed solution enters reactor 10 via conduit 14, and purified aqueous terephthalic acid solution having a relatively lower 4-carboxybenzaldehyde content exits reactor 10 at the bottom as an effluent via conduit 16. Fixed particulate catalyst bed 18 is constituted by first catalyst layer 20, second catalyst layer 22, and optional, third catalyst layer 24.

First catalyst layer 20, in turn, is constituted by a particulate carrier, such as active carbon, containing a metal of Group VIII of the Periodic Table of Elements having a single electron in its outermost orbital when in ground state. The metals contemplated for this purpose are ruthenium, rhodium, and platinum. The preferred metal is rhodium. The metal loadings of the active carbon carrier are the same as those discussed hereinabove in connection with the method aspects of this invention.

The second catalyst layer 22 is also constituted by a particulate carrier, such as active carbon, and contains palladium in the same amounts as those discussed hereinabove in connection with the method aspects of this invention.

The optional third catalyst layer 24 is constituted by a particulate carrier, e.g., active carbon and rhodium, the latter being present in an amount of about 0.01 to about 2 weight percent, based on the total weight of the catalyst and calculated as elemental metal, preferably in an amount of about 0.5 weight percent, as mentioned hereinabove.

As will be apparent to those skilled in this art, the present invention, in a further aspect thereof, can also be utilized for production of benzoic acid, a commercially significant compound useful, inter alia, as a food preservative, as a mordant in calico printing, and as an intermediate for the manufacture of benzoates, benzoyl compounds, dyes and the like. To that end, and aqueous solution of 4-carboxybenzaldehyde is contacted in a pressure vessel, and in the presence of hydrogen, with a particulate catalyst containing one of the aforementioned Group VIII metals having a single electron in its outermost orbital. The reaction conditions for this purpose are the same as those described hereinabove for the purification of aqueous terephthalic acid solutions except that there is no need to pass the aqueous solution through a bed or layer of palladium-on-carbon catalyst.

As described hereinabove, carbon monoxide is generated concurrently with the decarbonylation of 4-carboxybenzaldehyde to benzoic acid. In this particular instance, the carbon monoxide is separated from the resulting aqueous solution and benzoic acid is recovered therefrom in any convenient manner.

The present invention is illustrated further by the following Examples.

EXAMPLE 1: Hydrogenation of Aqueous Crude Terephthalic Acid Solution in a Layered Catalyst Bed A pilot plant reactor of the down-flow type and equipped with a fixed catalyst bed one inch in diameter and 6.5 inches in length was used. The catalyst bed was constituted by a particulate commercial palladium-on-carbon catalyst (40 grams; 0.5 weight percent Pd; Engelhard) alone or by an upper particulate layer of rhodium-on-carbon catalyst (4 grams; 0.5 weight percent Rh) and a lower particulate layer of the same commercial palladium-on-carbon catalyst (40 grams). The rhodium-on-carbon catalyst was prepared from rhodium nitrate as a precursor, at a pH value of 2 in water, and using North American active carbon G-201 as support. All catalysts were hot washed and aged for 72 hours in an autoclave in the presence of terephthalic acid and hydrogen. The reactor was operated at a temperature of about 280° C. (535° F.) and at hydrogen partial pressures of 50, 100, and 150 psi. The total reactor pressures were about 975, 1025 and 1075 psig, respectively. Crude terephthalic acid slurry containing about 12 weight percent terephthalic acid and about 2,700 ppm 4-carboxybenzaldehyde was fed to the reactor at a feed rate of 1.6 kg of solution per hour. The observed results are compiled in Table I below.

TABLE I

Hydrogenation of 4-CBA

| Catalyst Bed | Reaction Product | $H_2$ Pressure, psi | | |
|---|---|---|---|---|
| | | 50 | 100 | 150 |
| Pd/C only | TOL, ppm | 3227 | 3696 | 3990 |
| (40 grams) | BA, ppm | 705 | 673 | 631 |
| | TOL/BA | 4.58 | 5.49 | 6.32 |
| Rh/C (4 g) | TOL, ppm | 2433 | 2852 | 3371 |
| Pd/C (40 g) | BA, ppm | 1595 | 1587 | 1581 |
| | TOL/BA | 1.53 | 1.80 | 2.13 |

The foregoing results demonstrate that in a layered catalyst bed having an upper layer of rhodium-on-carbon and a lower layer of palladium-on-carbon the amount of benzoic acid produced is increased, and the amount of 4-carboxybenzaldehyde converted to p-toluic acid is decreased, as compared to a catalyst bed containing only palladium-on-carbon.

EXAMPLE 2: Selectivity of Pd/C and Rh/C Catalysts

The selectivity of a commercial palladium-on-carbon catalyst (4 grams; 0.5 weight percent Pd; Engelhard) and a rhodium-on-carbon catalyst prepared as in Example 1, above (4 grams; 0.5 weight percent rhodium-on-carbon) were compared in a titanium autoclave of one gallon capacity. Crude terephthalic acid (about 290 grams) was dissolved in water (about 1190 grams) at about 277° C. (about 530° F.), placed in the autoclave, and hydrogen was added thereto to provide a $H_2$ partial pressure, at reactor temperature, of about 50 psi. Thereafter the palladium-on-carbon or rhodium-on-carbon catalyst was added to the autoclave.

An initial sample of the terephthalic acid solution was taken just before the addition of the catalyst and thereafter at predetermined intervals. The samples were analyzed by liquid chromatography, and the amounts of 4-carboxybenzaldehyde, p-hydroxymethylbenzoic acid (HMBA), TOL and BA present in the samples were determined.

The results are compiled in Table II below.

TABLE II

Autoclave Tests

| Time, hr | Commercial 0.5% Pd/C Catalyst Reaction Product, ppm | | | | | 0.5% Rh/C Catalyst Reaction Product, ppm | | | | |
|---|---|---|---|---|---|---|---|---|---|---|
| | 4-CBA | HMBA | TOL | BA | Total | 4-CBA | HMBA | TOL | BA | Total |
| 0 | 2610 | 99 | 582 | 379 | 3670 | ~2500 | 190 | 587 | ~400 | 3677 |
| 0.5 | 581 | 1295 | 1337 | 1047 | 4260 | 560 | 275 | 662 | 2256 | 3753 |
| 1 | 170 | 1410 | 1651 | 1106 | 4377 | 148 | 125 | 665 | 2616 | 3554 |
| 2 | 64 | 952 | 2167 | 1215 | 4398 | 31 | 133 | 796 | 3003 | 3963 |
| 3 | 49 | 715 | 2548 | 1524 | 4836 | 11 | 91 | 785 | 2950 | 3837 |
| 4 | 34 | 437 | 2710 | 1509 | 4690 | 1 | 68 | 786 | 3048 | 3893 |

The foregoing results illustrate the surprising ability of rhodium-on-carbon catalyst to decarbonylate 4-carboxybenzaldehyde at highly reducing conditions without an adverse change in the 4-carboxybenzaldehyde reduction rate as compared to a commercial palladium-on-carbon catalyst.

EXAMPLE 3: Comparison of Pd/C Catalyst Bed With a Layered Catalyst Bed Containing Equal Amounts of Rh/C and Pd/C A bed of commercial palladium-on-carbon catalyst (10 grams; 0.5 weight percent Pd; Engelhard) and a bed constituted by an upper layer of rhodium-on-carbon catalyst (5 grams, 0.5 weight percent Rh) and a lower layer of palladium-on-carbon catalyst (5 grams; 0.5 weight percent palladium-on-carbon; Engelhard) were used to hydrogenate a crude terephthalic acid aqueous solution in a down-flow pilot plant reactor.

Figure 3:
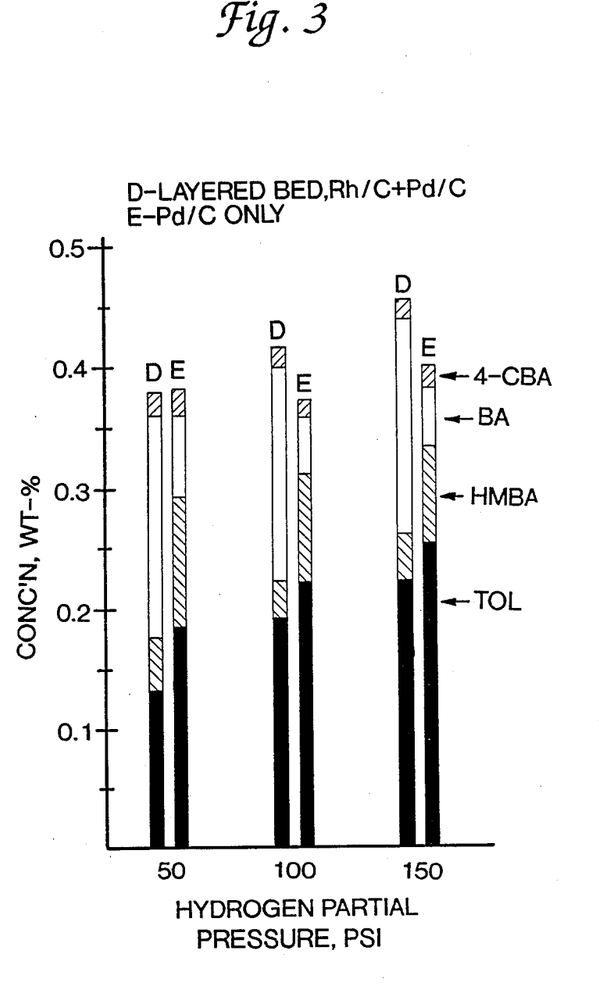
FIG. 3 is a bar graph showing the conversion obtained in a layered catalyst bed at a Rh-to-Pd mol ratio of about 1:1 and a comparison with conversion at the same conditions in an unlayered Pd/C catalyst bed.

The feed solution to the reactor contained about 12 weight percent terephthalic acid and about 2,700 ppm 4-carboxybenzaldehyde. The reactor conditions were as follows:

Temperature: 280° C. (535° F.)
Pressure: 975 psig, 1025 psig & 1075 psig
$H_2$ Partial Press.: 50 psi, 100 psi & 150 psi
Residence Time: 0.63 minutes The amounts of 4-carboxybenzaldehyde, benzoic acid, p-hydroxymethylbenzoic acid and p-toluic acid in the reactor effluent were monitored. The observed amounts are presented graphically in FIG. 3. The calculated p-toluic acid-to-benzoic acid (TOL/BA) weight ratios are presented in Table III below.

TABLE III

TOL/BA Weight Ratios at Varying Hydrogen Partial Pressures

| Catalyst-Bed | TOL/BA at $H_2$ Partial Press., psi | | |
|---|---|---|---|
| | 50 | 100 | 150 |
| Pd/C only | 2.61 | 4.75 | 5.2 |
| Rh/C and Pd/C in equal weight layers | 0.85 | 1.07 | 1.27 |

The data in the foregoing Table show that substantially lower p-toluic acid-to-benzoic acid weight ratios are maintained in the reactor effluent when a layered catalyst bed having an upper rhodium-on-carbon layer and a lower palladium-on-carbon layer is used.

EXAMPLE 4: Comparison of Pd/C Catalyst Bed Performance With That of Layered Rh/C and Pd/C Catalyst Bed In a manner similar to Example 3, above, a down-flow pilot plant reactor was used to compare the performance of a 55-gram catalyst bed containing only a commercial palladium-on-carbon catalyst (0.5 weight percent Pd; Engelhard) with a catalyst bed containing two layers containing an upper layer of 5 grams of rhodium-on-carbon catalyst (0.5 weight percent Rh) and a lower layer of 50 grams of a commercial palladium-on-carbon catalyst (0.5 weight percent Pd; Engelhard). All catalysts were aged in a titanium autoclave for 72 hours in the presence of terephthalic acid and hydrogen.

Figure 2:
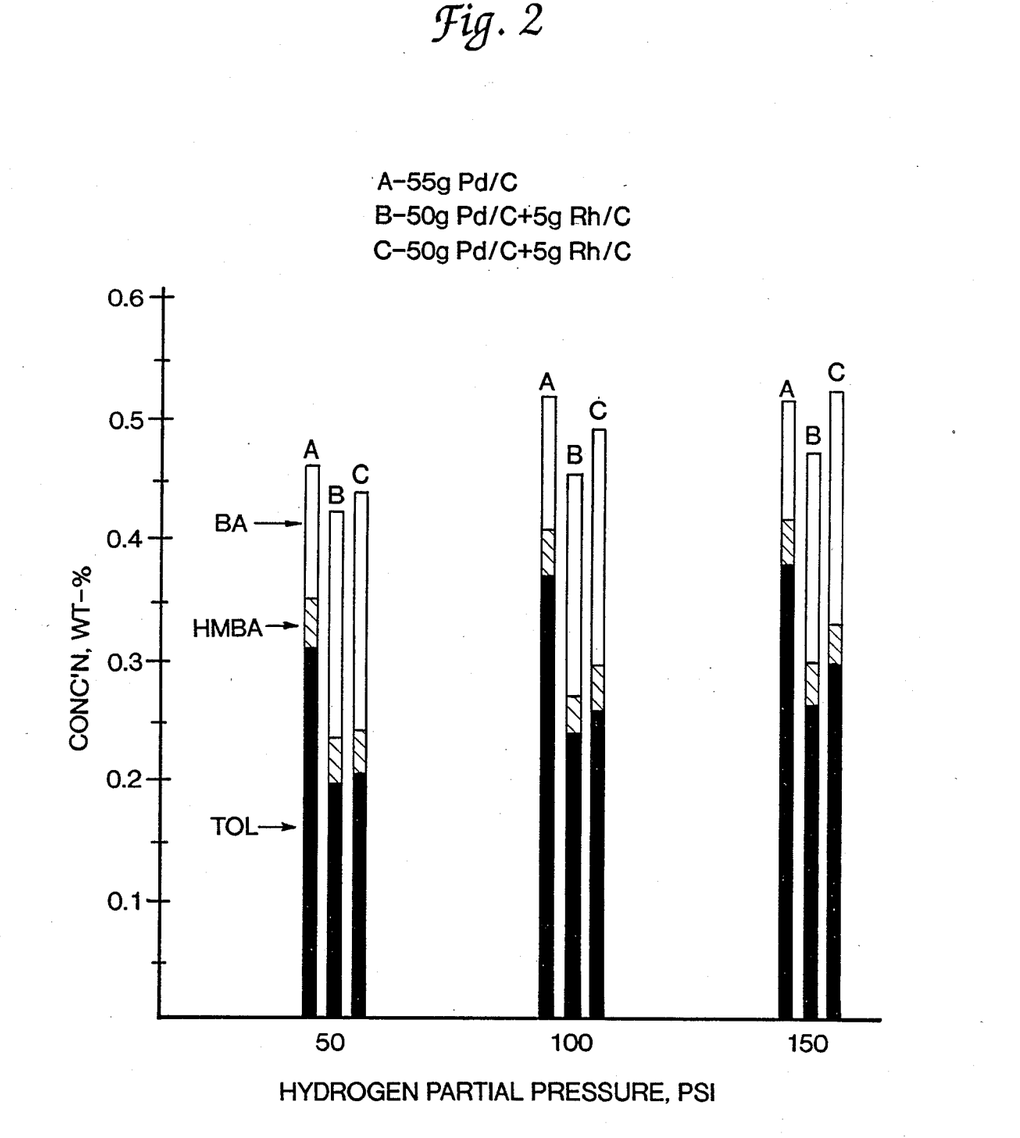
FIG. 2 is a bar graph showing the conversion of 4-carboxybenzaldehyde to benzoic acid at various hydrogen partial pressures in a layered catalyst bed having a first layer of Rh/C catalyst and a second layer of Pd/C catalyst at a Rh-to-Pd mol ratio of about 1:10 in the catalyst bed and a comparison with conversion at the same conditions in an unlayered Pd/C catalyst bed.

The reactor feed solution contained about 12 weight percent terephthalic acid, and about 2,700 ppm 4-carboxybenzaldehyde. The reactor conditions were as follows:

Temperature: 280° C. (530° F.)
Pressure: 975 psig, 1025 psig & 1075 psig
$H_2$ Partial Press.: 50 psi, 100 psi & 150 psi
Residence Time: 3.5 minutes The amounts of benzoic acid, p-hydroxymethylbenzoic acid, and p-toluic acid were monitored in the reactor effluent. The observed results are compiled in FIG. 2. Each bar shown in FIG. 2 represents the average of four samples taken one-half hour apart and analyzed three times each.

The calculated p-toluic acid-to-benzoic acid weight ratios are presented in Table IV below.

TABLE IV

TOL/BA Weight Ratios at Different Processing Conditions

| Catalyst-Bed | TOL/BA at $H_2$ Partial Press., psi | | |
|---|---|---|---|
| | 50 | 100 | 150 |
| Pd/C (Run A) | 2.96 | 3.28 | 3.77 |
| Rh/C and Pd/C in 1:10 weight ratio (Run B) | 1.09 | 1.35 | 1.51 |
| Rh/C and Pd/C in 1:10 weight ratio (Run B) | 1.04 | 1.34 | 1.57 |

The data presented in FIG. 2 demonstrate that as the p-toluic acid content of the reactor effluent decreases when a layered rhodium-on-carbon and palladium-on-carbon catalyst bed is used, there is a corresponding increase in the benzoic acid content of the effluent.

EXAMPLE 5: Conversion of CO to Methane by Rh/C Catalyst Under Reducing Conditions The effect of a rhodium-on-carbon catalyst (0.5 weight percent Rh) on the conversion of carbon monoxide to methane was compared with that of a conventional palladium-on-carbon catalyst (0.5 weight percent palladium-on-carbon) used for the purification of aqueous terephthalic acid solutions.

Both catalyst were first aged for 72 hours in a one gallon titanium autoclave in the presence of terephthalic acid and hydrogen. Thereafter, aliquots of the respective catalysts (4 grams) were contacted for four hours in the autoclave maintained at about 277° C. (about 530° F.) with an aqueous terephthalic acid solution (290 grams of crude terephthalic acid; 1160 grams of water). A mixture of hydrogen and carbon monoxide (100 psi $H_2$ and 20 psi CO) at reaction temperature was also present in the autoclave.

After the aforementioned four-hour interval, heat to the autoclave was turned off, the autoclave was permitted to cool to about ambient temperature, and gas samples withdrawn from the autoclave. The withdrawn gas samples were then analyzed for carbon monoxide, carbon dioxide, and methane. The results from these analyses are set forth in Table V below.

TABLE V

| | Hydrocarbon Content of Gas Samples | | |
|---|---|---|---|
| | Mol % | | |
| Catalyst | CO | $CO_2$ | $CH_4$ |
| Pd/C | 15.64 | 0.56 | 0.01 |
| Rh/C | 14.45 | 1.53 | 2.27 |

The foregoing analysis shows that only the Rh/C catalyst converted significant amounts of carbon monoxide to methane.

EXAMPLE 6: Improvement of Optical Properties and Fluorescence Characteristics

Example 6 involves 24-hour per day operations in a commercial unit for the continuous purification of crude terephthalic acid, which had been formed by the continuous liquid-phase oxidation of p-xylene with an oxygen-containing gas in a solvent at an elevated temperature and pressure and in the presence of an oxidation catalyst in a commercial unit. The specific solvent, oxygen-containing gas, catalyst, temperature, pressure and solvent residence time, which had been employed in the oxidation, are all within the classes and ranges described therefor hereinabove. Furthermore, each of the aforesaid gas, solvent, catalyst, temperature, pressure, and solvent residence time was essentially the same in each run.

Example 6 also involves two sets of runs. In both sets of runs, the aqueous solvent, temperature, pressure and overall space velocity (weight of crude terephthalic acid per weight of total catalyst per hour) employed in the purification reaction are all within the classes and ranges described therefor generally hereinabove. Furthermore, each of the aforesaid solvent temperature, pressure and overall space velocity was essentially the same in each run. In one of the sets of runs, Set A, the bed of catalyst particles contained only palladium-on-carbon catalyst particles containing 0.5 weight percent of palladium calculated as elemental palladium and having a total surface area of about 1000 $m^2$/gm and having a particle size of 4 to 8 mesh. In the second set of runs, Set B, the same bed was employed except that 10 weight percent of the total amount of palladium-on-carbon catalyst particles in the bed was removed from the top of the bed and replaced by a layer of rhodium-on-carbon catalyst particles containing 0.5 weight percent of rhodium, calculated as elemental rhodium, and having a total surface area of about 1000 $m^2$/gm and having a particle size of 4 to 8 mesh.

In each of Sets A and B an aqueous solution of crude terephthalic acid was introduced into the top portion of the purification reactor and flowed downward from the top to the bottom of the catalyst bed. In addition, each of Sets A and B involved at least 4 consecutive days of 24-hour per day operation.

The data illustrates that for Set A the resulting purified terephthalic acid had an average optical density of 0.09, and average b*value of 1.18, and an average fluorescence index of 0.95. For Set B the resulting purified terephthalic acid had an average optical density of 0.08, an average b*value of 0.81, and an average fluorescence index of 0.79, indicating a substantial improvement of the optical and fluorescence properties of the purified terephthalic acid from Set B relative to that from Set A.

The foregoing specification and the accompanying examples are intended as illustrative and are not to be taken as limiting. Still other variations in processing conditions and layered catalyst bed arrangements are possible and will readily present themselves to those skilled in the art.

Having described the invention, what is claimed is:

1. A method for the purification of crude terephthalic acid, comprising:

passing an aqueous solution of said crude terephthalic acid, at a temperature of from about 100° C. to about 350° C. and at a pressure sufficient to maintain the solution substantially in the liquid phase, through a particulate catalyst bed and in the presence of hydrogen; said particulate catalyst bed being a layered bed that includes a first catalyst layer supported on an active carbon carrier and containing a metal of Group VIII of the Periodic Table of Elements having a single electron in its outermost orbital when in the ground state, and a lower catalyst layer containing palladium supported on an active carbon carrier; said solution being first passed through said first layer and thereafter being passed through said second layer; and thereafter cooling the hydrogenated aqueous solution to effect separation of the resulting purified terephthalic acid from said solution by crystallization.

2. The method of claim 1 wherein the solution is maintained at a temperature of about 245° C. to about 300° C., and wherein hydrogen is present in an amount about twice the amount stoichiometrically required.

3. The method of claim 1 wherein the space velocity of the aqueous terephthalic acid solution through the catalyst bed is about 5 hours$^{-1}$ to about 25 hours$^{-1}$.

4. The method of claim 3 wherein the space velocity of the aqueous terephthalic acid solution through the catalyst bed is about 10 hours$^{-1}$ to about 15 hours$^{-1}$.

5. The method of claim 1 wherein the residence time of the aqueous terephthalic acid solution in said first catalyst layer is about ½ to about 1/100 of the total residence time of the aqueous terephthalic acid solution in the particulate catalyst bed.

6. The method of claim 1 wherein said Group VIII metal is rhodium.

7. The method of claim 6 wherein rhodium is present in the first catalyst layer in a concentration of about 0.01 to about 2 percent by weight, based on the weight of the catalyst in the first catalyst layer and calculated as elemental rhodium.

8. The method of claim 1 wherein the crude terephthalic acid contains up to about 10,000 parts of 4-carboxybenzaldehyde per million parts by weight of terephthalic acid and hydrogen is present in the particulate catalyst bed in an amount at least equal to that stoichiometrically required to effect a predetermined decrease in the 4-carboxybenzaldehyde content.

9. A method for the purification of crude terephthalic acid, comprising:

hydrogenating an aqueous solution of said crude terephthalic acid, at a temperature of about 100° C. to about 350° C. and at a pressure sufficient to maintain the solution substantially in the liquid phase, in a particulate catalyst bed; said particulate catalyst bed being a layered bed that includes a first catalyst layer supported on an active carbon carrier and containing a metal of Group VIII of the Periodic Table of Elements having a single electron in its outermost orbital when in the ground state, and a second catalyst layer containing palladium supported on an active carbon carrier; said hydrogenation being carried out with attendant carbon monoxide generation, while maintaining in the liquid effluent from the particulate catalyst bed p-toluic acid-to-benzoic acid weight ratio of less than about 2.5, and hydrogen being present in the particulate catalyst bed in an amount at least equal to that stoichiometrically required to effect a predetermined decrease in the 4-carboxybenzaldehyde content and to convert at least a portion of the generated carbon monoxide to a hydrocarbon moiety; and thereafter cooling the hydrogenated aqueous solution to effect separation of relatively pure terephthalic acid from said solution by crystallization.

10. The method of claim 9 wherein the p-toluic acid-to-benzoic acid weight ratio is maintained in the range of from about 1.5 to about 0.5.

11. A layered catalyst bed suitable for hydrogenation of a relatively impure aqueous solution of crude terephthalic acid containing 4-carboxybenzaldehyde which comprises:

a first catalyst layer constituted by a particulate active carbon carrier containing a metal of Group VIII of the Periodic Table of Elements having a single electron in its outermost orbital when in the ground state; and a second catalyst layer constituted by a particulate active carbon carrier containing palladium.

12. The layered catalyst bed of claim 11 wherein said first catalyst layer constitutes a minor portion of the catalyst bed and said second catalyst layer constitutes a major portion of the catalyst bed.

13. The layered catalyst bed of claim 11 wherein said Group VIII metal is on the particulate carrier in an amount of about 0.01 to about 2 percent by weight, based on the combined weight of the carrier and metal and calculated as elemental metal.

14. The layered catalyst bed of claim 11 wherein said Group VIII metal is rhodium and is present in an amount of about 0.5 percent by weight, based on the combined weight of the carrier and metal and calculated as elemental metal.

15. The layered catalyst bed of claim 11 wherein said Group VIII metal is ruthenium.

16. The layered catalyst bed of claim 11 wherein said Group VIII metal is rhodium.

17. The layered catalyst bed of claim 11 wherein said Group VIII metal is platinum.

18. The layered catalyst bed of claim 11 wherein the first catalyst layer is at least about 25 millimeters thick.

19. The layered catalyst bed of claim 11 wherein the volumetric ratio of the first catalyst layer to the second catalyst layer is about 0.001 to about 1.

20. The layered catalyst bed of claim 11 wherein the volumetric ratio of the first catalyst layer to the second catalyst layer is about 0.1.

21. The layered catalyst bed of claim 11 wherein the mol ratio of said Group VIII metal in the first catalyst layer to palladium in the second catalyst layer is about 1 to about 0.001.

22. The layered catalyst bed of claim 11 wherein the mol ratio of said Group VIII metal in the first catalyst layer to palladium in the second catalyst layer is about 0.1.

23. The layered catalyst bed of claim 11 wherein the first catalyst layer is constituted by a rhodium-on-carbon catalyst and the second catalyst layer is constituted by a palladium-on-carbon catalyst.

24. The layered catalyst bed of claim 23 wherein the mol ratio of rhodium to palladium in the catalyst bed is about 1 to about 0.001.

25. The layered catalyst bed of claim 23 wherein the mol ratio of rhodium to palladium in the catalyst bed is about 0.1.

26. The layered catalyst bed of claim 23 wherein rhodium concentration in the first catalyst layer is about 0.01 to about 2 percent by weight of the respective catalyst and wherein palladium concentration in the second catalyst layer is about 0.01 to about 2 percent by weight of the respective catalyst.

27. The layered catalyst bed of claim 23 wherein rhodium concentration in the first catalyst layer is about 0.5 percent by weight of the respective catalyst and wherein palladium concentration in the second catalyst layer is about 0.5 percent by weight of the respective catalyst.

28. The layered catalyst bed of claim 11 further including a third catalyst layer downstream from said second catalyst layer and constituted by a particulate active carbon carrier containing rhodium.

29. The layered catalyst bed of claim 28 wherein the third catalyst layer is at least about 50 millimeters thick.

30. A method for purification of relatively impure terephthalic acid containing up to about 10,000 parts per million, by weight of 4-carboxybenzaldehyde which comprises the steps of:

passing in aqueous solution of said impure terephthalic acid, at a temperature of about 100° C. to about 350° C. and at a pressure sufficient to maintain the solution in liquid phase, through a particulate catalyst bed and in the presence of hydrogen; said particulate catalyst bed being a layered bed that includes a first catalyst layer supported on an active carbon carrier and containing a metal of Group VIII of the Periodic Table of Elements having a single electron in its outermost orbital when in ground state, and a lower catalyst layer containing palladium supported on an active carbon carrier; said solution being first passed through said first layer and thereafter being passed through said second layer; the hydrogen being present in the particulate catalyst bed in an amount at least equal to that stoichiometrically required to effect a predetermined decrease in the 4-carboxybenzaldehyde content, wherein the residence time of the aqueous terephthalic acid solution in said first catalyst layer is about ½ to about 1/100 of the total residence time of the aqueous terephthalic acid solution in the particulate catalyst bed; and thereafter cooling the hydrogenated aqueous solution to effect separation of relatively pure terephthalic acid from said solution by crystallization.

* * * * *

UNITED STATES PATENT OFFICE
CERTIFICATE OF CORRECTION

Patent No. __4,892,972__                    Dated __January 9, 1990__

Inventor(s) __Hobe Schroeder & David E. James__

It is certified that error appears in the above-identified patent and that said Letters Patent is hereby corrected as shown below:

| Col. | Line | |
|---|---|---|
| 1 | 65 | "(X, Y. and Z)" should read --(X, Y, and Z)-- |
| 2 | 1-3 | "... $R_\lambda x_\lambda, ... R_\lambda y_\lambda, R_\lambda z_\lambda$..." should read $$X = \sum_{400}^{700} R_\lambda \bar{x}_\lambda, \quad Y = \sum_{400}^{700} R_\lambda \bar{y}_\lambda, \quad Z = \sum_{400}^{700} R_\lambda \bar{z}_\lambda,$$ -- |
| 2 | 27 | "in gray" should read --is gray-- |
| 2 | 30 | "b*-value" should read --b*-values-- |
| 4 | 36 | "the generated" should read --The generated-- |
| 7 | 15 | "guage" should read --gauge-- |
| 7 | 17 | "the hydrogenaton" should read --The hydrogenation-- |
| 9 | 35 | "3,584,039; to" should read --3,584,039 to-- |
| 10 | 2 | "reuqirement" should read --requirement-- |
| 13 | 14 | "catalyst" should read --catalysts-- |

Signed and Sealed this

Eleventh Day of December, 1990

Attest:

HARRY F. MANBECK, JR.

*Attesting Officer*              *Commissioner of Patents and Trademarks*